United States Patent [19]

Johnson

[11] 4,262,116

[45] Apr. 14, 1981

[54] ENLARGED HETERO-RING PROSTACYCLIN ANALOGS

[75] Inventor: Roy A. Johnson, Kalamazoo, Mich.

[73] Assignee: The Upjohn Company, Kalamazoo, Mich.

[21] Appl. No.: 932,981

[22] Filed: Aug. 11, 1978

Related U.S. Application Data

[60] Division of Ser. No. 819,856, Jul. 28, 1977, Pat. No. 4,123,441, which is a continuation-in-part of Ser. No. 725,546, Sep. 22, 1976, abandoned, which is a continuation-in-part of Ser. No. 716,960, Aug. 23, 1976, abandoned.

[51] Int. Cl.³ .................................. C07D 307/93
[52] U.S. Cl. ........................ 542/426; 260/345.2; 542/429
[58] Field of Search .................... 542/426, 429; 260/345.2, 346.22

[56] References Cited

U.S. PATENT DOCUMENTS 4,125,713 11/1978 Nelson .......................... 542/426

Primary Examiner—Nicky Chan
Attorney, Agent, or Firm—Robert A. Armitage

[57] ABSTRACT

Prostaglandin ($PG_1$) derivatives having (1) a 5-keto feature, for example

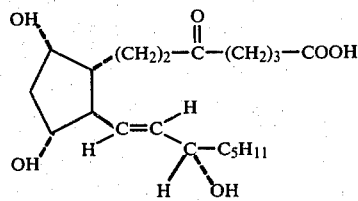

or (2) a 9-deoxy-5,9-epoxy feature together with a 4-halo or 5-hydroxy feature, for example

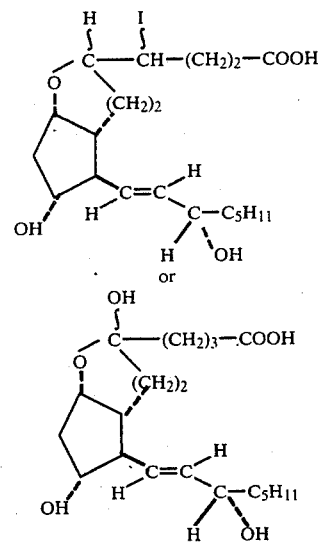

or a 4,5-didehydro feature, for example in an enol ether of the formula

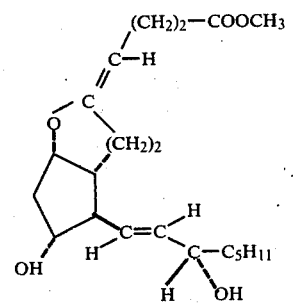

said derivatives having pharmacological activity. Processes for preparing them and the appropriate intermediates are disclosed.

13 Claims, No Drawings

ENLARGED HETERO-RING PROSTACYCLIN ANALOGS

CROSS REFERENCE TO THE RELATED APPLICATIONS

This application is a division of Ser. No. 819,856, filed July 28, 1977, now issued as U.S. Pat. No. 4,123,441, which was a continuation-in-part of then copending application Ser. No. 725,546, filed Sept. 22, 1976, since abandoned, which was a continuation-in-part of then copending application Ser. No. 716,960, filed Aug. 23, 1976, since abandoned.

The essential material for this application, including the background of the invention, the disclosure of the invention, and the description of the preferred embodiments, including Preparations and Examples, is incorporated by reference from issued U.S. Pat. No. 4,123,441, under the provisions of M.P.E.P. 608.01 (p).

BACKGROUND OF THE INVENTION

This invention relates to prostaglandin derivatives and to a process for preparing them.

The prostaglandins and analogs are well-known organic compounds derived from prostanoic acid which has the following structure and atom numbering:

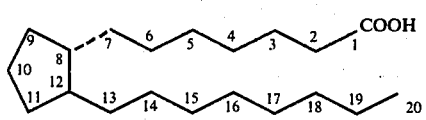

As drawn hereinafter the formulas represent a particular optically active isomer having the same absolute configuration as PGE$_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

For background on prostaglandins, see for example Bergstrom et al., Pharmacol. Rev. 20, 1 (1968). For related compounds see Pace-Asciak et al., Biochem. 10, 3657 (1971). Related compounds are described in a publication on 6-keto-prostaglandin F$_{1\alpha}$ by Pace-Asciak, J. Am. Chem. Soc. 98, 2348 (1976) and a publication on "PGX" (6,9α-oxido-9α,15α-dihydroxyprosta-(Z)5, (E)13-dienoic acid) by E. J. Corey et al., J. Am. Chem. Soc. 99, 20006 (1977).

Some of the compounds of this invention may be regarded as analogs of prostacyclin and prostacyclin-type compounds.

Prostacyclin, an organic compound related to prostaglandins, is (5Z)-9-deoxy-6,9α-epoxy-Δ$^5$-PGF$_1$ and is represented by the formula

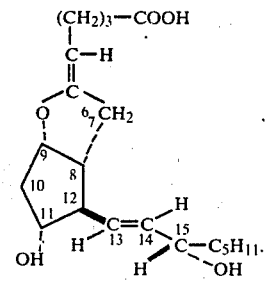

For its synthesis and structure see for example R. A. Johnson et al., J. Am. Chem. Soc. 99, 4182 (1977) and Prostaglandins 12, 915 (1976), and E. J. Corey et al., cited above. For some of its biological properties and uses see the references cited in the Johnson references. Prostacyclin is referred to as "PGI$_2$", see Anonymous, Prostaglandins 13, 375 (1977).

SUMMARY OF THE INVENTION

It is the purpose of this invention to provide novel products having pharmacological activity. It is a further purpose to provide processes for preparing these products and their intermediates.

Accordingly, there is provided a compound of the formula:

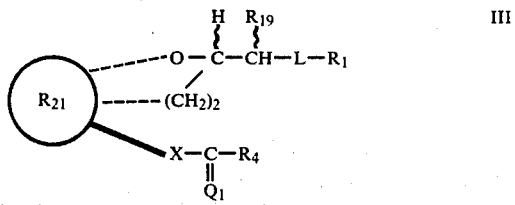

In compounds of formula III, Q$_1$ is

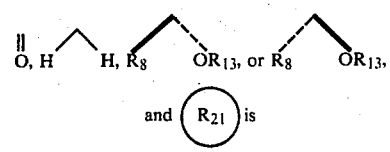

and $R_{21}$ is

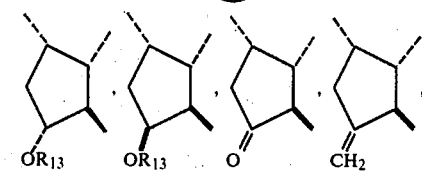

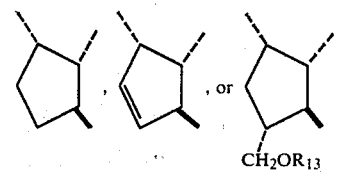

In formula III, R$_{13}$ is (a) hydrogen, (b) tetrahydropyranyl, (c) tetrahydrofuranyl, (d) 1-ethoxyethyl, (e) a group of the formula

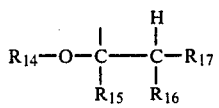

wherein $R_{14}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{15}$ and $R_{16}$ are the same or different, being hydrogen, alkyl of one to 4 carbon atoms, inclusive, phenyl or phenyl substituted with one, 2, or 3 alkyl of one to 4 carbon atoms, inclusive, or, when $R_{15}$ and $R_{16}$ are taken together —(CH$_2$)a— or —(CH$_2$)b—O—(CH$_2$)c— wherein a is 3, 4, or 5, b is one, 2, or 3, and c is one, 2, or 3 with the proviso that b plus c is 2, 3, or 4, and wherein $R_{17}$ is hydrogen or phenyl, or (f) carboxyacyl including

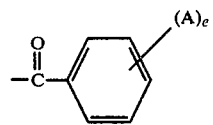

(a')

wherein "A" is alkyl of one to 4 carbon atoms, inclusive, bromo, phenylalkyl of 7 to 10 carbon atoms, inclusive, or nitro, and "e" is zero to 5, inclusive, provided that not more than two A's are other than alkyl, and that the total number of carbon atoms in the A's does not exceed 10 carbon atoms,

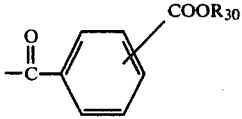

(b')

wherein $R_{30}$ is alkyl of one to 4 carbon atoms, inclusive,

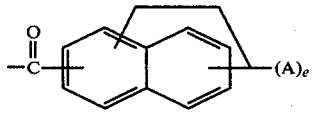

(c')

wherein "A" and "e" are as defined above, or $$-\overset{O}{\underset{\|}{C}}-R_{31}$$ (d')

wherein $R_{31}$ is alkyl of one to 7 carbon atoms, inclusive; wherein L is
(1) —(CH$_2$)d—C(R$_2$)$_2$—
(2) —O—CH$_2$—Y— or
(3) —CH=CH—
wherein d is zero to 5, $R_2$ is hydrogen, methyl, or fluoro, being the same or different with the proviso that one $R_2$ is not methyl when the other is fluoro, and Y is a valence bond, —CH$_2$—, or —(CH$_2$)$_2$—,
wherein $R_1$ is
(1) —COOR$_3$
(2) —CH$_2$OH
(3) —CH$_2$N(R$_9$)(R$_{18}$)

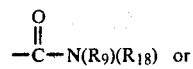

(4)

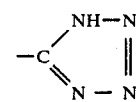

(5)

wherein $R_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

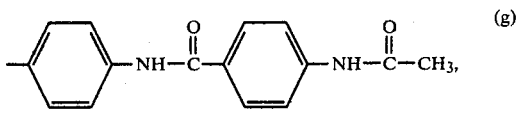

(g)

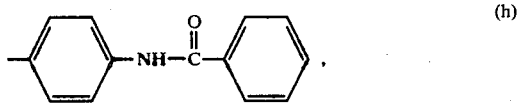

(h)

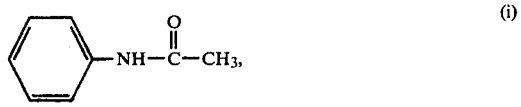

(i)

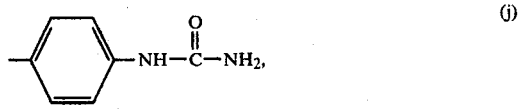

(j)

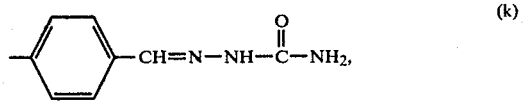

(k)

(l)

(m)

wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl, or (n) a pharmacologically acceptable cation, wherein $R_9$ is hydrogen, methyl, or ethyl, and wherein $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive, wherein $R_4$ is

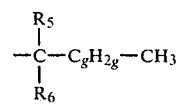

(1)

-continued

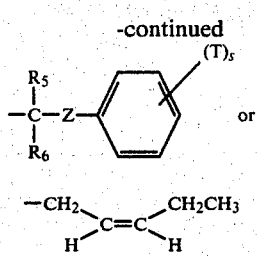

wherein $C_gH_{2g}$ is alkylene of one to 9 carbon atoms, inclusive, with one to 5 carbon atoms, inclusive, in the chain between —$CR_5R_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6$— and the phenyl ring; wherein T is alkyl of one to 4 carbon atoms, inclusive, fluoro chloro, trifluoromethyl, or —$OR_7$—
wherein $R_7$ is alkyl of one to 4 cirbon atoms, inclusive, and s is zero, one, 2, or 3, with the proviso that not more than two T's are other than alkyl and when s is 2 or 3 the T's are either the same or different;
wherein $R_{19}$ is chloro, bromo, or iodo,
wherein X is
(1) trans-CH=CH—
(2) cis-CH=CH—
(3) —C≡C— or
(4) —$CH_2CH_2$—, and
wherein wavy line (~) indicates attachment in alpha or beta configuration.

An example of the halo compounds of formula III is represented by the formula

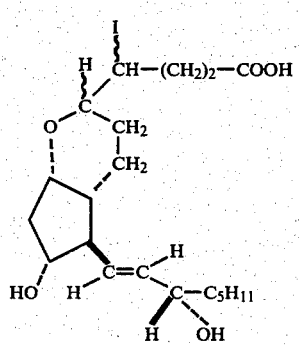

VII and named 4ξ-iodo-9-deoxy-5ξ,9α-epoxy-$PGF_1$.

I claim:

1. A compound of the formula

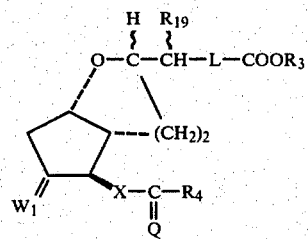

wherein $W_1$ is α-OH:β-H, α-H:β-OH, oxo, methylene, α-H:β-H, α-$CH_2OH$:β-H;
wherein L is —$(CH_2)_d$—$C(R_2)_2$,
wherein d is zero to 5, $R_2$ is hydrogen, methyl, or fluoro, being the same or different with the proviso that one $R_2$ is not methyl when the other is fluoro,
wherein Q is oxo, α-H:β-H, α-OH:β-$R_8$ or α-$R_8$:β-OH
wherein $R_8$ is hydrogen or alkyl of one to 4 carbon atoms, inclusive,
wherein $R_3$ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl of one to 4 carbon atoms, inclusive,
(g) p-[p-(acetamido)benzamido]phenyl,
(h) p-benzamidophenyl,
(i) p-acetamidophenyl,
(j) p-phenylurea,
(k) p-benzaldehyde semicarbazone,
(l) β-naphthyl,
(m) $CH(R_{11})$—CO—$R_{10}$,
wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl, or
(n) a pharmacologically acceptable cation;
wherein $R_4$ is
(1) —$CR_5R_6$—$C_gH_{2g}$—$CH_3$
(2) —$CR_5R_6$—Z—(Ph)
(3) cis-$CH_2$—CH=CH—$CH_2CH_3$
wherein $C_gH_{2g}$ is alkylene of one to 9 carbon atoms, inclusive, with one to 5 carbon atoms, inclusive, in the chain between —$CR_5R_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between —$CR_5R_6$ and the (Ph); wherein (Ph) is phenyl or phenyl substituted by (T)s, wherein T is alkyl of one to 4 carbon atoms, inclusive, fluoro, chloro, trifluoromethyl, or —$OR_7$—, wherein $R_7$ is alkyl of one to 4 carbon atoms, inclusive, and s is zero, one, 2, or 3, with the proviso that not more than two T's are other than alkyl and when s is 2 or 3 the T's are either the same or different;
wherein $R_{19}$ is chloro, bromo, or iodo; and
wherein X is
(1) trans-CH=CH—
(2) cis-CH=CH—
(3) —C≡C— or
(4) —$CH_2CH_2$—.

2. A compound according to claim 1, wherein W is α-OH:β-H.

3. A compound according to claim 2, wherein L is —$(CH_2)_n$—, n being 2, 3, or 4, wherein Q is oxo or α-OH:β-$R_8$, and wherein $R_8$ is hydrogen, methyl, or ethyl, and wherein $R_4$ is n-pentyl, 1,1-dimethylpentyl, 1,1-difluoropentyl, phenoxymethyl or phenylethyl.

4. A compound according to claim 3, wherein X is trans-CH=CH—.

5. A compound according to claim 4, wherein $R_3$ is —$CHR_{11}$—CO—$R_{10}$.

6. 4ξ-Iodo-9-deoxy-5ξ,9α-epoxy-PGF$_1$, p-phenylphenacyl ester, compounds according to claim 5.

7. A compound according to claim 4, wherein $R_3$ is hydrogen, alkyl of one to 12 carbon atoms, inclusive, or a pharmacologically acceptable cation.

8. 4ξ-Iodo-9-deoxy-5ξ,9α-epoxy-PGF$_1$, compounds according to claim 7.

9. 4ξ-Iodo-9-deoxy-5ξ,9α-epoxy-PGF$_1$, methyl ester, compounds according to claim 7.

10. 4ξ-Bromo-9-deoxy-5ξ,9α-epoxy-PGF$_1$, methyl ester, compounds according to claim 7.

11. 4ξ-Iodo-9-deoxy-5ξ,9α-epoxy-15-keto-PGF$_1$, methyl ester, compounds according to claim 7.

12. 4ξ-Iodo-9-deoxy-5ξ,9α-epoxy-15-deoxy-PGF$_1$, methyl ester, compounds according to claim 7.

13. 4ξ-Iodo-9-deoxy-5ξ,9α-epoxy-17-phenyl-18,19,20-trinor-PGF$_1$, methyl ester, compounds according to claim 1.

* * * * *